United States Patent [19]
Barlocher et al.

[11] 3,937,626
[45] Feb. 10, 1976

[54] AGENTS FOR REGULATING PLANT METABOLISM

[75] Inventors: Toni Barlocher, Oberwil, Switzerland; Edith Ebert, Lorrach-Stetten, Germany

[73] Assignee: Ciba-Geigy Corporation, Ardsley, N.Y.

[22] Filed: Apr. 3, 1974

[21] Appl. No.: 457,523

Related U.S. Application Data

[62] Division of Ser. No. 288,640, Sept. 13, 1972, Pat. No. 3,818,034.

[52] U.S. Cl. ............................ 71/92; 71/68; 71/74; 71/76; 71/78
[51] Int. Cl.² ............................................. A01N 9/22

[58] Field of Search ................................. 71/92, 74

[56] References Cited
UNITED STATES PATENTS

| | | | |
|---|---|---|---|
| 2,895,817 | 7/1959 | Luckenbaugh | 71/92 |
| 3,418,334 | 12/1968 | Stoffel | 71/92 |
| 3,541,111 | 11/1970 | Gerike | 71/74 |

*Primary Examiner*—Glennon H. Hollrah
*Attorney, Agent, or Firm*—Harry Falber

[57] ABSTRACT

2,4,5-trioxo-imidazolidine-3-carboxylic acid amides possess plant metabolism influencing properties. They may be used for regulating fruit abscission.

6 Claims, No Drawings

AGENTS FOR REGULATING PLANT METABOLISM

This is a division of application Ser. No. 288,640, filed on Sept. 13, 1972, now U.S. Pat. No. 3,818,034.

The present invention relates to 2,4,5-trioxo-imidazolidine-3-carboxylic acid amides, a process for their manufacture, also to agents for regulating plant metabolism which contain these new compounds as active substances, and to a process for regulating plant metabolism, in particular for regulating the abscission of fruit and senescence, which comprises the use of the new active substances or the agents which contain them.

The new 2,4,5-trioxo-imidazolidine-3-carboxylic acid amides correspond to the formula

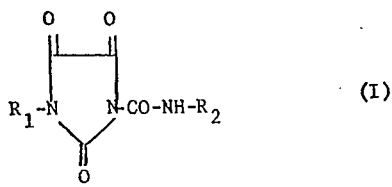

(I)

wherein $R_1$ represents an alkyl or alkenyl radical with at most 4 carbon atoms or a phenyl radical which is optionally substituted by chlorine, nitro, lower alkyl containing at most 4 carbon atoms, and $R_2$ represents an alkyl or alkenyl radical with at most 4 carbon atoms.

By the alkyl radicals in formula I are meant methyl, ethyl, n-propyl, isopropyl, n-butyl, isobutyl, sec.butyl and tert.butyl. Among these radicals, particularly the methyl and ethyl group form the alkyl moiety of a phenyl radical. By alkenyl radicals in formula I are meant straight-chain or branched propenyl or butenyl radicals. The allyl and methallyl radicals are preferred.

The new compounds of the formula I may also be termed parabanic acid derivatives. According to the present invention they are manufactured by cyclising a urea of the formula II $$R_1-NH-CO-NH_2 \quad (II)$$

with an oxalyl halide to give a 2,4,5-trioxo-imidazolidine derivative of the formula III

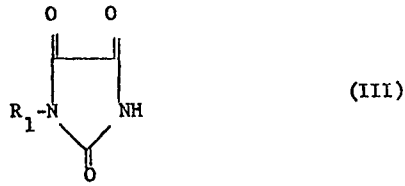

(III)

and subsequently reacting this product with an isocyanate of the formula IV $$R_2NCO \quad (IV)$$

in the presence of an organic base.

$R_1$ and $R_2$ in the formulae II to IV have the same meanings as given under formula I.

The reactions are carried out in solvents or diluents which are inert towards the reactants. The reaction temperatures are in the range from 10°C to 110°C.

The following may be used as solvents or diluents which are inert towards the reactants: aliphatic and aromatic hydrocarbons and halogenated hydrocarbons, such as benzene, toluene, xylenes, petroleum ether, chlorobenzene, methylene chloride, ethylene chloride, chloroform, carbon tetrachloride, ethers and ethereal solvents, such as dialkyl ether, dioxan, tetrahydrofuran, and acetonitrile; preferably aromatic hydrocarbons such as benzene and toluene or acetonitrile are used.

The reaction of a urea of the formula II with an oxalyl halide may take place in the presence of inorganic bases. An organic base is necessary as initiator for the introduction of the $CONHR_2$ group. Tertiary amines may be used as organic bases, e.g. trialkylamines, such as triethylamine, trimethylamine, dialkylanilines, pyridine and pyridine bases.

The following Examples will serve to illustrate the invention. Further derivatives of the formula I which were manufactured according to the process described in the Examples are to be found in the succeeding Table.

EXAMPLE 1 a. 272.3 g of N-phenylurea are dissolved in 1.5 liters of tetrahydrofuran. The solution is heated to 50°C and slowly treated with 171 ml of oxalyl chloride, in the course of which the reaction temperature should not exceed 65°C. Stirring is continued for 1 hour at room temperature and then for 4 hours under reflux. The reaction mixture is evaporated and the residue is recrystallised from isopropanol to give 1-phenyl-2,4,5-trioxo-imidazolidine (m.p. 214°–216°C).

b. 19 g of 1-phenyl-2,4,5-trioxo-imidazolidine are suspended in 100 ml of benzene. Upon addition of 11.2 ml of methyl isocyanate and 0.5 ml of triethylamine the mixture is allowed to undergo complete reaction over the course of 12 hours by stirring it at room temperature. The reaction mixture is cooled to 10°C and the analytically pure precipitated 1-phenyl-3-methylcarbamoyl-2,4,5-trioxo-imidazolidine is filtered with suction and thoroughly washed with benzene. The product melts at 110°C. (Compound No. 1).

EXAMPLE 2 a. 23 g of sodium are reacted in 400 ml of absolute ethanol to give the sodium alcoholate. 74.1 g of methyl urea are added at room temperature and the mixture is stirred until a clear solution forms. While stirring is continued, 146.14 g of oxalic diethyl ester are slowly added dropwise without external cooling, so that the reaction temperature fluctuates between 25° and 30°C. Upon completion of addition, the reaction mixture is stirred for 1 hour at room temperature and 110 ml of conc. hydrochloric acid is slowly added dropwise so that the reaction temperature does not exceed 30°C. The reaction mixture is stirred for 1 hour, then filtered. The filtrate is concentrated until a slurry substance is obtained which is filtered with suction and dried at 50°C. The resulting 1-methyl-2,4,5-trioxo-imidazolidine is recrystallised from isopropanol; m.p. 153°–154°C.

b. 12.8 g of 1-methyl-2,4,5-trioxo-imidazolidine are suspended in 100 ml of benzene. Upon addition of 12.4 g of allyl isocyanate and 0.5 ml of triethylamine stirring is continued for 2 hours at room temperature and for 4 hours at 40°C. Upon cooling, the 1-methyl-3-allylcarbamoyl-2,4,5-trioxo-imiazolidine is filtered with suction and carefully washed with benzene. After recrystallisation from chloroform the product melts at 106°–110°C (compound No. 2).

The following Table lists further compounds of the formula I

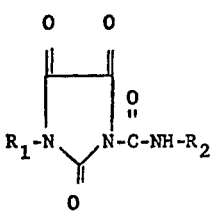

which were manufactured by the processes described in the preceding Examples.

| Compound No. | R₁ | R₂ | Melting Point |
|---|---|---|---|
| 3 | methyl | methyl | 129°(decomp.) |
| 4 | methyl | ethyl | 104°(decomp.) |
| 5 | methyl | n-propyl | 114°–118° |
| 6 | methyl | isopropyl | 108°–114° |
| 7 | methyl | n-butyl | 113°–117° |
| 8 | ethyl | methyl | 87°–90° |
| 9 | isopropyl | n-butyl | oil |
| 10 | sec.butyl | t-butyl | oil |
| 11 | ethyl | n-butyl | oil |
| 12 | ethyl | allyl | oil |
| 13 | ethyl | n-propyl | oil |
| 14 | allyl | isopropyl | oil |
| 15 | $O_2N$–⟨Cl-phenyl⟩– | ethyl | semi-crystalline |
| 16 | Cl–⟨CH₃-phenyl⟩– | ethyl | semi-crystalline |

The active substances of the formula I influence the growth of plant parts above and below the soil in various ways; they are not phytotoxic in conventional application concentrations and have a slight toxicity to warm blooded animals. The active substances do not bring about any morphological changes or damage which might lead to the death of the plant. The compounds are non-mutagenic and their action differs from that of a herbicidal active substance and a fertiliser.

The new active substances of the formula I influence in particular the vegetative plant growth and fruit development, as well as the development of abscission tissues between stem and leaf or between stem and fruit. It is thereby possible to detach fruit of all kinds, e.g. citrus fruit, stone fruit, pomaceous fruit, nuts, berries, grapes, bananas, pineapples, tomatoes or oleaginous fruit, without applying any great force either manually or with the aid of machines specially developped for the purpose.

The damage which is customarily inflicted on the leaves and branches of the trees and bushes during harvesting by vigorously shaking them, as well as by plucking the fruit, is very largely avoided.

On the other hand, by applying the active substances in a specific concentration it is also possible to provoke leaf sheeding in certain cultivated plants, such as cotton, soya, ornamental bushes, green beans and green peas, a factor which is also of economic importance. Tests also proved that a thinning out of blossom and fruit occurs in fruit trees.

The compounds according to the invention also regulate the growth of plants. In the case of monocotyledons, an increase in the tillering was observed accompanied by a simultaneous decrease in the growth in length. In dicotyledons, the cited compounds effect an inhibition of the terminal growth without damage being caused to the leaves of the plants. This is of practical importance, for example, in combating undesirable side-shoots in tobacco plants. Experience proves that it is necessary to sever or remove these side-shoots in order to avoid loss of quality or quantity in the leaf yield. Various ornamental plants, e.g. azaleas and chrysanthemums are pruned by hand, i.e. the leading shoot is cut off of pruned in order that the plant may branch. The cited compounds can also be used for this purpose in order to inhibit or kill the still young terminal buds.

The extent and nature of the action are dependent upon the most diverse factors which vary from one kind of plant to another, in particular on the application concentration, the time of application with regard to the development stage of the plant, and on the fruit. Thus, for example, plants whose fruit is utilised or processed are treated immediately after blossoming or at an appropriate interval of time before harvesting.

The active substances are applied in the form of solid or liquid agents both on parts of plants above the soil and in or on the soil. Application to parts of plants above the soil is preferred, for which purpose solutions or aqueous dispersions are best suited. Besides solutions and dispersions, dusts, granules and tracking agents are also suitable for the treatment of the soil.

ANALOGOUS TEST I - ABSCISSION OF FRUIT

In Florida, single branches of citrus trees of the indicated variety and which carried at least 12–50 ripe fruit, were sprayed with active substance concentrations of 0.4% and 0.2%. Seven days after the application the plucking force of 10 similarly treated fruit was determined with the aid of a spring balance and the mean value calculated from the 10 measurements [W. C. Wilson and C. H. Hendershott, Proc. Am. Soc. Hort. Science 90, 123–125 (1967)]. The active substances of the formula I in this test effected the reductions in plucking forms reproduced in the following Table. Two varieties of orange were used for the test:

1 = Valencia
2 = pine apple

| Active Substance | Concentration % | Force in kg | Oranges Variety |
|---|---|---|---|
| 1-methyl-3-ethylcarbamoyl-2,4,5-trioxo-imidazolidine | 0,2 | 8,2 | 2 |
|  | 0,4 | 7,1 | 2 |
| 1-methyl-3-n-propylcarbamoyl-2,4,5-trioxo-imidazolidine | 0,2 | + | 2 |
|  | 0,4 | + | 2 |
| 1-methyl-3-allylcarbamoyl-2,4,5-trioxo-imidazolidine | 0,2 | 7,1 | 2 |
|  | 0,4 | 5,8 | 2 |
| 1-methyl-3-methyl-carbamoyl-2,4,5-trioxo-imidazolidine | 0,2 | 8,1 | 1 |
|  | 0,4 | 7,6 | 1 |
| Control | — | 8,5 | 2 |

+The fruit hanging on the tree was so easily detached that no measurement was possible.

The fruit in all cases displayed no signs of damage; also no leaves and no green fruit were detached.

BIOLOGIAL TEST II

Test as Preservatives for Cut Flowers

Roses of the variety Dr. Verhagen (Holland) were used as test flowers. They were placed in the respective test solutions and kept in a conditioning cabinet of constant temperature (about 25°C) and at a relative humidity of about 80%. Their condition was checked each day. The Table indicates how many days the blossoms remained durable without losing petals or displaying signs of withering.

The active substances were not tested direct in water, but in a stock solution buffered to pH 3.4 which contained "Irgasan" as fungicide. These roses were in each container and three containers in each case contained the same solution. The durability in the stock solution containing no active substances is given as comparison. The active substances were added on a rule in a concentration of 50 ppm and formulated as wettable powders.

| Active Substance | Conc. ppm | Durability in Days |
|---|---|---|
| 1-methyl-3-methylcarbamoyl-2,4,5-trioxo-imidazolidine | 50 | 6,5 |
| 1-methyl-3-ethylcarbamoyl-2,4,5-trioxo-imidazolidine | 50 | 9 |
| 1-methyl-3-n-propylcarbamoyl-2,4,5-trioxo-imidazolidine | 50 | 9 |

| Active Substance | Conc. ppm | Durability in Days |
|---|---|---|
| 1-methyl-3-isopropylcarbamoyl-2,4,5-trioxo-imidazolidine | 50 | 8 |
| 1-methyl-3-allylcarbamoyl-2,4,5-trioxo-imidazolidine | 50 | 8 |
| 1-methyl-3-n-butylcarbamoyl-2,4,5-trioxo-imidazolidine | 50 | 8 |
| 1-methyl-3-methylcarbamoyl-2,4,5-trioxo-imidazolidine | 50 | 6,5 |
| 1-phenyl-3-methylcarbamoyl-2,4,5-trioxo-imidazolidine | 50 | 7 |
| Control : $H_2O$ (pH 3,4-+fungicide) | — | 3 |

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms:
 dusts, tracking agents, granules, coated granules, impregnated granules and homogeneous granules.

Liquid forms:
 a. active substances which are dispersible in water: wettable powders, pastes, emulsions;
 b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

The particle size of the carriers for dusts is advantageously up to about 0.1 mm, for tracking agents from about 0.075 to 0.2 mm, and for granules 0.2 mm or larger. The concentrations of active substance in the solid forms are from 0.5% to 80%.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water in any concentration desired. They consist of active substance, carrier, optionally additives which stabilize the active substance, surface-active substances and anti-foam agents and, optionally solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of napthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfonated fatty alcohol glycol ethers, the sodium salt of oleoyl ethionate, the sodium salt of oleoyl methyl tauride, ditertiary acetalene glycols, dialkyl dilauryl ammonium chloride and fatty acid alkali and alkaline earth metal salts.

Suitable anti-foam agents are silicones.

The active substances are so mixed, ground sieved and strained with the additives mentioned above that, in wettable powders, the solid particle size of from 0.02 to 0.04 and in pastes, of 0.03 is not exeeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulfoxide, N,N-dialkylated amides, N-oxides of amines, especially trialkylamines, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substances or several active substances are dissolved in suitable organic solvents, mixtures of solvents or in water. Aliphatic and aromatic hydrocarbons, chlorinated derivatives thereof, alkyl napthalenes and mineral oils alone or mixed with each other, can be used as organic solvents. The solutions should contain the active substances in a concentration ranging from 1% to 20%. These solutions may be applied either with the aid of a propellant gas (as spray) or with special sprayers (as aerosol). The agents described according to the invention can be mixed with other biocidally active substances or agents. Thus in order to broaden the activity spectrum the new agents may contain, for example insecticides, fungicides, bactericides, fungistatics, bacteriostatics or nematocides, in addition to the cited compounds of formula I. The agents according to the invention may also contain plant fertilizers, trace elements etc.

The active substances of the formula I can, for example, be formulated as follows. The parts denote parts by weight.

Granules

The following substances are used to manufacture 5% granules:

5 parts of 1-ethyl-3-allylcarbamoyl-2,4,5-trioxo-imidazolidine,
0.25 parts of epichlorohydrin,
0.25 parts of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable Powder

The following constituents are used to manufacture (a) a 40%, (b) a 50%, (c) a 25%, and (d) a 10% wettable powder:

a. 40 parts of 1-methyl-3-allylcarbamoyl-2,4,5-trioxo-imidazolidine
   5 parts of sodium lignin sulphonate
   1 part of sodium dibutylnapthalenesulphonate
   54 parts of silicic acid;

b. 50 parts of 1-methyl-3-methylcarbamoyl-2,4,5-trioxo-imidazolidine
   5 parts of alkylarylsulphonate ("Tinovetin B")
   10 parts of calcium lignin sulphonate
   1 part of Champagne chalk/hydroxyethyl cellulose mixture (1:1)
   20 parts of silicic acid
   14 parts of kaolin;

c. 25 parts of 1-ethyl-3-methylcarbamoyl-2,4,5-trioxo-imidazolidine
   5 parts of sodium oleylmethyltauride
   2.5 parts of naphthalenesulphonic acid/formaldehyde condensate
   0.5 parts of carboxymethyl cellulose
   5 parts of neutral potassium aluminium silicate
   62 parts of kaolin;

d. 10 parts of 1-methyl-3-isopropylcarbamoyl-2,4,5-trioxo-imidazolidine
   3 parts of a mixture of the sodium salts of saturated fatty alcohol sulphates
   5 parts of napthalenesulphonic acid/formaldehyde condensate
   82 parts of kaolin.

The active substances are intimately mixed in suitable mixers with the additives and ground in appropriate mills and rollers. Wettable powders are obtained which can be diluted with water to give suspensions of any desired concentration. These suspensions can be used e.g. for removing undesirable side-shoots, for the tillering of grass or for the rooting of cuttings.

Emulsion Concentrate

To manufacture 25% emulsion concentrates a. 25 parts of 1-ethyl3-n-butylcarbamoyl-2,4,5-trioxo-imidazolidine
   5 parts of a mixture of nonylphenolpolyoxyethylene and calcium dodecylbenzenesulphonate
   70 parts of xylene, b. 25 parts of 1-phenyl-3-methylcarbamoyl-2,4,5-trioxo-imidazolidine
   10 parts of a mixture of nonylphenolpolyoxyethylene and calcium dodecylbenzenesulphonate
   65 parts of cyclohexanone are mixed together. This concentrate can be diluted with water to suitable concentrations. These emulsions are suitable for thinning out blossoms and fruit, for accelerating the ripening of fruit and for promoting the detachment of fruit and leaves.

We claim:

1. A composition for regulating plant metabolism in the nature of promoting fruit abscission comprising as active ingredient, an effective non-phytotoxic amount of a compound of the formula

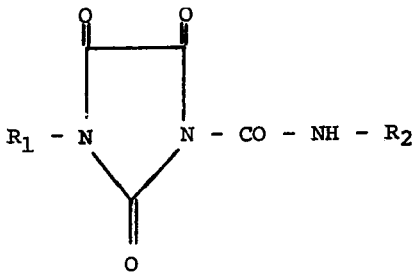

wherein $R_1$ represents alkyl or alkenyl each of up to 4 carbon atoms or phenyl optionally substituted by chlorine, nitro or alkyl of 1 to 4 carbon atoms, and $R_2$ represents alkyl or alkenyl each of up to 4 carbon atoms, together with a suitable inert carrier therefor.

2. The composition of claim 1, wherein in said active ingredient $R_1$ represents methyl, ethyl, isopropyl, sec. butyl, allyl or phenyl optionally substituted by chlorine, nitro, methyl or ethyl, and $R_2$ represents alkyl of 1 to 4 carbon atoms or allyl.

3. The composition of claim 1, wherein said active ingredient is 1-methyl-2,4,5-trioxoimidazolidine-3-carboxylic-acid-n-propylamide.

4. A process for regulating plant metabolism in the nature of promoting fruit abscission which comprises applying to said plant an effective non-phytotoxic amount of a 2,4,5-trioxo-imidazolidine-3-carboxylic acid amide according to claim 1.

5. The process of claim 4, wherein the acid amide corresponds to the formula of claim 2.

6. The process of claim 4, wherein said acid amide is 1-methyl-2,4,5-trioxo-imidazolidine-3-carboxylic-acid-n-propylamide.

* * * * *

UNITED STATES PATENT AND TRADEMARK OFFICE
CERTIFICATE OF CORRECTION

PATENT NO. : 3,937,626
DATED : February 10, 1976
INVENTOR(S) : Toni Barlocher and Edith Ebert It is certified that error appears in the above-identified patent and that said Letters Patent are hereby corrected as shown below:

The following should be inserted in the heading:

Claims priority, application Switzerland

September 30, 1971, No. 14214/71

Signed and Sealed this

Nineteenth Day of October 1976

[SEAL]

*Attest:*

RUTH C. MASON
*Attesting Officer*

C. MARSHALL DANN
*Commissioner of Patents and Trademarks*